United States Patent [19]

Plummer

[11] Patent Number: 5,705,152
[45] Date of Patent: Jan. 6, 1998

[54] ANTIMICROBIAL COMPOSITION

[75] Inventor: Nigel Plummer, Swansea, United Kingdom

[73] Assignee: Interprise Limited, West Glamorgan, United Kingdom

[21] Appl. No.: 301,135

[22] Filed: Sep. 6, 1994

Related U.S. Application Data

[63] Continuation of Ser. No. 30,391, Apr. 8, 1993, abandoned.

[30] Foreign Application Priority Data

Oct. 26, 1990 [GB] United Kingdom ............... 9023337

[51] Int. Cl.$^6$ .................................. A01N 63/00
[52] U.S. Cl. ................... 424/93.45; 424/93.44; 424/93.4; 424/195.1; 435/252.1; 435/252.9
[58] Field of Search .......... 435/252.1, 252.9; 424/195.1, 93.4, 93.44, 93.45

[56] References Cited

U.S. PATENT DOCUMENTS

| | | | |
|---|---|---|---|
| 4,874,704 | 10/1989 | Boudreaux et al. | 435/252.9 |
| 5,296,221 | 3/1994 | Mitsuoka et al. | 424/935 |
| 5,302,388 | 4/1994 | Doyle et al. | 424/93 C |
| 5,302,391 | 4/1994 | Hamane et al. | 424/195.1 |
| 5,322,686 | 6/1994 | Grahn et al. | 424/93 H |
| 5,332,579 | 7/1994 | Umbdenstock | 424/639 |
| 5,340,577 | 8/1994 | Nisbet et al. | 424/93.21 |
| 5,372,810 | 12/1994 | Onishi et al. | 424/93.4 |
| 5,378,459 | 1/1995 | Grahn et al. | 424/93 J |
| 5,413,785 | 5/1995 | Nanji | 424/93.45 |
| 5,439,678 | 8/1995 | Debrogosz et al. | 424/93.45 |

FOREIGN PATENT DOCUMENTS

| | | | |
|---|---|---|---|
| 0033584 | 8/1981 | European Pat. Off. | 435/252.9 |
| 0 302 300 | 2/1989 | European Pat. Off. | |
| 2101880 | 1/1970 | Germany . | |
| 61260023 | 11/1968 | Japan . | |
| 0007699 | 2/1982 | Japan | 424/93 D |
| 0108385 | 5/1986 | Japan | 435/252.9 |
| 0130680 | 6/1987 | Japan | 435/252.9 |
| 1293215 | 2/1987 | U.S.S.R. | 435/252.9 |

OTHER PUBLICATIONS

ATCC Catalogue of Bacteria & Bacteriophages, 18th Ed., p. 242 1992.
Basic Medical Microbiology, 3rd Ed., Little, Brown and Co., Boston/Toronto, pp. 537 and 538, 1986.
Souane et al. (1987) Kor. J. Appl. Microbiol. Bioeng. 15:150-7.
Ade Tumbi, et al., "Medical Hypotheses," vol. 12 (3) Nov. 1983, pp. 227–237.
Tynecka, et al., "Acta Microbiologica Polenica," vol. 5 (22), No. 1, pp. 51–62, 1973.
Weber, et al., "Plenta Medica," vol. 58, Oct. 1992, pp. 389–484.
Tynecka, Z. et al., "The Fungistatic activity of Garlic (Allium sativum L.) in vitro", Ann Univ Mariae Curie Skodowska Med. 30:5–13 (1975).
Uchida, Y, et al., "The characteristics of the antibacterial activity of garlic (author's transl)", Jpn J. Antibiot. 28(4): (Aug. 1975) abs.
Giminez, M.A. et al., "Bevista Argentina de Miaobio. Logica," vol. 20, #1, 1988, pp. 17–24 & Translation.
Uchida, Y., et al., "The Japanese Journal of Antibiotics," vol. 28, #4, 1975 (Aug.), pp. 638–642 & Translation.
Paszewski, A., et al. "Ann. Univer. Mariae Curie–Skyodowska." vol. 33, 1978, #54 Section D, pp. 415–422.
Adetumbi, M.A. et al, "Medical Hypotheses," vol. 12(3), Nov. 1983, pp. 227–237.

*Primary Examiner*—Chhaya D. Sayala
*Attorney, Agent, or Firm*—Klauber & Jackson

[57] ABSTRACT

An antimicrobial composition comprising an antimicrobial material derived from the plant family Allium together with non-pathogenic microorganisms of at least one species, in which the antimicrobial material is isolated from the plant material in such a way (for example, by freeze-drying of whole cloves) that the material comprises alliin and alliinase and is substantially free of allicin. The composition is useful for combatting pathogenic microorganisms in animal gastrointestinal tract or for treatment of silage.

12 Claims, No Drawings

ANTIMICROBIAL COMPOSITION

This application is a continuation of application Ser. No. 08/030,391, filed Apr. 8, 1993 now abandoned.

The present invention is concerned with antimicrobial compositions, and the use thereof in the health/nutrition industry as dietary supplements, and as silage treatment agents.

It is known that antimicrobial materials can be extracted from the plant family Allium (which includes edible plants such as onions, chives, shallots, leek and garlic). The antimicrobial properties of garlic are well documented and garlic juice has been shown to inhibit the growth of a variety of pathogenic micro-organisms including Staphylococcus, Klebsiella, Proteus, *Escherichia coli* and Salmonella.

The antibacterial activity of garlic is attributed largely to a compound known as allicin. About 0.24% (w/w) of each garlic clove consists of a compound known as alliin which is a non-odoriferous derivative of the amino acid cysteine. Intracellularly separated from the alliin in the garlic clove is an enzyme known as alliinase.

When the garlic clove is crushed, the alliinase comes into contact with the alliin to produce the odorous, unstable, water-soluble substance known as allicin (diallyl thiosulphinate).

Allicin decomposes readily to form a variety of intermediate products ultimately consisting of a mixture of allyl sulphides. This degradation process occurs at room temperature but is much faster at elevated temperatures. The degradation products of allicin (i.e. the diallyl sulphides) have very little antimicrobial activity.

The mode of action of the allicin is largely unknown, but it is thought to act by blocking important metabolic enzymes, particularly those containing reactive SH groups. Alternatively, it may act by disrupting the microbial cell metabolism by interfering with protein function or by binding to cysteine and glutathione and inhibiting their activity.

The antifungal activity of garlic appears to be a combination of the effects of allicin and a specifically antifungal breakdown product of allicin known as ajoene. It has been found that lipid synthesis in *C. albicans* can be completely inhibited in the presence of garlic extract.

Dried (or freeze-dried) garlic powder is also known, which is prepared by crushing garlic cloves and then drying the crushed material. This results in reaction of alliin with alliinase to produce allicin.

We have now discovered that improved antimicrobial materials can be obtained from plant sources if special procedures are adopted which have been found to avoid reaction between alliin and alliinase.

According to the invention, there is provided an antimicrobial composition which comprises dried non-pathogenic microorganisms in combination with an antimicrobial material derived from the plant family Allium, the antimicrobial material comprising alliin and alliinase and being substantially free of allicin.

Known antibiotic compositions used to treat gastrointestinal disorders tend to have broad spectrum activities and act on both pathogenic and beneficial organisms in the gastrointestinal tract, leaving the gut susceptible to reinfection by pathogenic organisms. In contrast, the antimicrobial composition according to the invention acts selectively against pathogenic organisms, attacking pathogenic microorganisms but not beneficial microorganisms.

The antimicrobial composition according to the invention preferably comprises a carrier which is substantially unaffected by culture growth of pathogenic microorganisms thereon (which carrier may be the antimicrobial material, the non-pathogenic microorganisms, or another material which does not substantially interact with either said antimicrobial material or with said non-pathogenic microorganisms).

The composition according to the invention may be used for therapeutic treatment of certain microbial mediated diseases, particularly those of the gastrointestinal tract, e.g. enteric disease caused by *E. coli*, rotavirus and *Candida spp* and microbially mediated diseases of the urinogenital tract, e.g. where *Candida albicans* is implicated, and/or for the improvement of the health and well being of the subject being treated.

The present invention encompasses the selective use of microorganisms of any of the genera Lactobacillus, Bifidobacteria, Enterococcus and Pedioccus in the antimicrobial composition according to the invention.

The microbial component of the composition of the present invention provides a source of beneficial microorganisms which will effectively compete with any potential pathogens present in the gastrointestinal tract, and should therefore be capable of colonizing the small intestine of the host when the composition is used for administration to animals.

The gastrointestinal tract of the neonatal animal is sterile at birth but it rapidly becomes colonized by the microorganisms prevailing in the natural environment. It is essential that the organisms that colonize the gastrointestinal tract at that stage are the beneficial organisms which will effectively prevent the establishment of pathogens. However, the pathogens tend to grow more rapidly than the beneficial organisms and this is one reason why disease occurs in young animals.

Preferably the microbial component present in the composition according to the invention comprises at least one strain of a host-specific, non-pathogenic Gram-positive bacteria which:

1. attaches to the epithelial tissue of the small intestine of the host;
2. is resistant to at least 3% (w/w) bile salts;
3. has a doubling time of less than two hours in vitro; and
4. is a homo- or hetero-fermentative lactic acid producer with greater than 40% by molarity of the acid produced thereby being lactic acid.

The microbial component preferably substantially retains its stability and characteristic features after being subjected to a typical production strategy of fermentation, centrifugation and spray- or freeze-drying. The microbial component is combined according to the invention with the antimicrobial material in such a way that allicin production is not triggered until the composition is put into use.

A preferred microbial component for use in the composition according to the invention is of the species *Lactobacilius acidophilus* or *Lactobacillus plantarum*.

The plant extract component of the composition according to the present invention is typically obtained either from the drying of substantially the entire bulb of the relevant Allium species (which includes many well known edible plants such as onions, chives, shallots, leeks and garlic). The preferred source of the plant extract is *Allium sativum* (garlic).

The antimicrobial activity of the antibacterial material present in the composition according to the invention has been found to be highly selective. We have found that there is no adverse effect on selected members of the beneficial lactobacillus microbial population of the gastrointestinal tract.

It is preferred that fresh substantially whole garlic cloves are freeze dried to produce garlic granules or powder, for use in the composition according to the invention. The freeze drying process entails the rapid freezing of the substantially whole cloves followed by gently drying at temperatures between −25 and −5 degrees Celsius.

In the composition according to the invention, more than one species of microorganism may be present. The dosage of microorganisms depends largely on the target host and the treatment required, but the number of microorganisms in any 24 hours period is typically from $1 \times 10^7$ to $1 \times 10^{12}$. The dosage of the antimicrobial material also depends upon the target host and treatment required, but the dosage of fresh garlic equivalent administered over a 24 hour period is generally between 1 and 10,000 mg. The formulation may be provided to animal patients in any suitable form, such as a powder, tablet, capsule or similar form, or an aqueous solution containing the formulation as an active ingredient.

According to the present invention there is also provided a method of therapeutic treatment which comprises administering to an animal, simultaneously or successively, an antimicrobial material derived from the plant family Allium, which comprises alliin and alliinase and is substantially free of allicin, and at least one species of non-pathogenic microorganisms, such that the antimicrobial material acts selectively against pathogenic microorganisms present in the animal.

There is further provided a kit for combatting pathogenic microorganisms in the gastrointestinal tract of animals or for treatment of silage, said kit comprising a first receptacle containing an antimicrobial material derived from the plant family Allium, and a second receptacle containing at least one species of non-pathogenic microorganisms, in which the antimicrobial material comprises alliin and alliinase and is substantially free of allicin.

It is also intended that lower dosage levels (subtherapeutic amounts) of the composition according to the present invention may be used in the animal feed industry as a growth promoting agent, similar to the way in which subtherapeutic levels of antibiotics are currently used to perform such a function.

The composition according to the invention may be used where physiological, emotional or environmental stresses are placed on the patient which profoundly alters the balance of the microflora. This may include events such as post-antibiotic therapy, post-drug therapy and menstruation in human cases, and weaning in the case of domestic animals.

In addition to its activity against pathogenic bacteria, the composition according to the invention has antiviral properties and in vitro activity against influenza B virus. This is particularly important in view of the fact that a large percentage of the cases of diarrhea in young animals have been attributed to strains of rotavirus rather than to bacterial sources.

Ensilage is a major way of adequately preserving forage as a winter feed. The ensilage process basically allows lactic acid bacteria to convert sugars in the forage to acids, notably lactic acid. The production of this acid and the resultant pH drop results in a material having a pH of about 4.0. The material stabilizes and further spoilage is prevented by the silage being kept in anaerobic/microaerophilic conditions.

A major problem in silage is aerobic spoilage which occurs when it is exposed to the air at the time of feeding the silage to the livestock.

This aerobic spoilage is mainly caused by yeasts and moulds which multiply to a large degree before the lactic fermentation of the silage has been completed. This higher population level is benign when the silage is anaerobic, but when exposed to the air, the yeast and mould population rapidly multiply, utilizing residual sugar and lactic acid, and producing ethanol and acetic acid, which is undesirable.

The addition of lactic acid cultures to forage to encourage and hasten the ensilage process is now well established. The species normally used is *Lactobacillus plantarum*. By adding the composition according to the invention at the time of ensilage, the proliferation of the yeast and mould population is dramatically reduced whilst not interfering with the desirable ensilage fermentation. The end result is that when opened to the air during feeding of the silage to the livestock, there is a much greater delay in the onset of aerobic spoilage.

The following Examples are given by way of illustration only.

EXAMPLE 1

Whole garlic cloves were peeled to remove the brittle outer skin. The clove was left entirely intact (cutting the scar causes some allicin to be produced). The cloves were then frozen to −30° C. Primary freeze drying took place with the product at temperatures between −25° C. and −5° C.

When the primary freeze drying phase was completed, the temperature of the garlic cloves rose rapidly to +20° C. where it remained whilst secondary drying took place to remove desorbed water. This took approximately 2 hours, the entire drying process taking between 12 and 24 hours.

The resulting freeze-dried powder contained 1.55% alliin and had allicin potency (as measured by the size of zone of inhibition of the yeast *Candida Albicans*) of 15 mm.

Similar results, but with slightly less allicin potency, were obtained by cutting off the scar at the end of each clove to accelerate moisture loss during the freeze-drying process.

Again similar results were obtained by cryogenically crushing, dicing or milling of the frozen whole cloves, reaction between alliin and alliinase being substantially prevented by ensuring that the temperatures did not exceed −20° C. at any point during the cryogenic treatment.

The results achieved using freeze-dried whole garlic cloves are compared with those from crushed garlic in the following table.

| | Alliin (Micrograms/gram Powder) | Allicin Potency (mm spread) |
|---|---|---|
| Whole cloves freeze dried (according to the invention) | 1.55% | 15 |
| Crushed garlic 4° C. 30 mins Freeze Dried | 0.42% | 13 |
| Crushed garlic 4° C. 2 hours Freeze dried | 0.11% | 12 |
| Crushed garlic 4° C. 24 hours Freeze dried | Trace | 9.5 |
| Crushed garlic 20° C. 30 mins Freeze dried | 0.04% | 11 |
| Crushed garlic 20° C. 2 hours Freeze dried | Trace | 10 |
| Crushed garlic 20° C. 24 hours Freeze dried | Trace | 6 |

The above table demonstrates the rapid reduction in the level of alliin after disintegration of a garlic clove, and the concomitant decrease on the allicin potency as demonstrated by a bioassay method against the yeast *Candida albicans*.

The results show that allicin is rapidly produced from alliin and alliinase even at low temperatures. Also the antimicrobial activity of the preparation is decreased after allicin is formed and this decrease is dependent both upon time and temperature.

In the extreme cases above, garlic cloves which were crushed and kept for 24 hours at 20° C. before freeze drying had only 40% of the activity of garlic which was freeze-dried as the whole clove.

The Allicin potency (measured in mm) was assayed as follows:

Equidistant wells were bored in agar plates containing MRS (de Mann, Rogosa and Sharpe) medium. The plates were then seeded with a lawn of Candida Albicans.

An overnight mixture of the organism was prepared and the agar plates were flooded with standardized concentrations of the mixture and the excess culture was removed. The lawns of the various cultures were allowed to dry and then the garlic preparations (at 20 mg/ml) were added to the wells in equal concentrations.

The efficacy, or allicin potency, was detected as a zone of clearing around the well containing the garlic and the comparative activities could be assessed by the diameters of the zones (in mm) in inhibition.

The test was repeated for several other microorganisms, using freeze-dried whole garlic cloves according to the invention, at 50 mg/ml; the results are given in the following table:

| Organism | Diameter of Zone (mm) |
| --- | --- |
| E. coli | 56 |
| C. albicans | 42 |
| E. faecium | No inhibition |
| S. aureus | 40 |
| L. acidophilus | No inhibition |
| L. plantarum | No inhibition |

This showed that the freeze dried garlic had a significant inhibitory effect on the growth of the pathogenic organisms viz. E. coli, C. albicans and Staph aureus. However, the freeze dried garlic preparation did not have any adverse effects on the growth of "beneficial" intestinal organisms such as L. acidophilus, E. faecium or L. plantarum and can therefore be combined therewith to produce compositions according to the invention.

The organisms L. acidophilus and L. plantarum referred to above were isolated from the pig's gut were identified and the Gram-positive organisms were selected for further study.

The chosen organisms were put through a screening procedure and five strains of Lactobacillus were finally selected on the basis of their performance. These strains were not fully identified but were:

Lactobacillus acidophilus

Lactobacillus delbruekii

Lactobacillus plantarum

Lactobacillus sp

Lactobacillus sp

On the basis of these results, the organisms were subjected to the production regime and two of the strains showed good survival through the process; these were the L. acidophilus and L. plantarum referred to above.

EXAMPLE 2

The Antimicrobial Effect of the Composition In Vitro

The effects of the composition were tested in vitro using the plate/well method previously described. The composition was prepared according to the formulation used for field trial studies and was added to the wells directly. The antimicrobial activity was tested against C. albicans (which was used as the reference organism for testing antimicrobial activity) and E. coli, which is a strain known to be pathogenic to pigs and so provides a good indication of the potential activity of the composition.

| Organism | Diameter of Zone (mm) |
| --- | --- |
| C. albicans | 15 |
| E. coli | 9 |
| L. acidophilus | No inhibition |
| L. plantarum | No inhibition |

The zones observed during this study were smaller than those observed previously because the garlic concentration (of the composition) was 20 mg/ml compared with the 50 mg/ml used in the previous study.

EXAMPLE 3

Effect of Strains of Lactobacillus on the growth of C. albicans In Vitro

It is very difficult to demonstrate the potentially inhibitory activity of Lactobacillus in the laboratory. However, a system has been developed which involves the growth of various strains of Lactobacillus at 30° C. for 24 hours and then spinning down to obtain the supernatants which are filter sterilized and used as the aqueous phase for fresh batches of media. The plates which were prepared were inoculated with a pathogenic strain of Candida and the effects of the Lactobacillus growth media on the growth of the yeast were observed.

The results are shown in the following table:

| Lactobacillus strain | Inhibition of Growth (%) |
| --- | --- |
| L 1 | 40 |
| L 4 | 58 |
| L 5 | 0 |
| L 6 | 69 |
| L 7 | 99 |
| L 8 | 99 |
| L 9 | 100 |
| L10 | 98 |
| L11 | 0 |
| Acidic pH | 63 |

As can be seen, using this modified in vitro method for assessing the inhibition of C. albicans, several strains of Lactobacillus can inhibit the growth of the pathogenic yeast.

EXAMPLE 4

Population Growth of Yeasts and Moulds of Grass Silage Exposed to Air for Feeding to Livestock

| | Number of Yeasts & Molds | |
| --- | --- | --- |
| | Immediately on Exposure to air | After 72 hrs Exposure to air |
| Freeze dried Alliin and Alliinase* (100 mg/kg) + Freeze dried Lactobacillus Plantarum* (1.0 × 10⁹/kg) | 5.0 × 10²/g | 6.5 × 10⁴/g |
| Freeze dried Lactobacillus Plantarum* Applied at 1.0 × 10⁹/kg) | 2.3 × 10⁴/g | 1.47 × 10⁷/g |
| Control | 1.9 × 10⁴/g | >2 × 10⁸/g |

*All treatments applied at time of ensiling.

All the above silages had a satisfactory fermentation profile with pH values ranging from 3.8–4.1.

Visually, the control sample was showing signs of mould growth at the end of 72 hours. The sample treated with *L. plantarum* alone was visually not as appealing as the sample with alliin-alliinase and *L. plantarum* applied together.

I claim:

1. An antimicrobial composition for inhibiting propagation of pathogenic microorganisms and promoting colonization of non-pathogenic microorganisms in the gastrointestinal tract of a human or non-human animal which comprises:
   (i) dried non-pathogenic microorganisms of the genera Lactobacillus, Enterococcus or Pediococcus, and having the following characteristics:
      (a) they can attach to the epithelial tissue of the small intestine of said animal;
      (b) they resist to at least 3% (w/w) bile salts;
      (c) they have a doubling time of less than two hours in vitro; and
      (d) they are homo- or heterofermentative lactic acid producers with greater than 40% by molarity of the acid produced thereby being lactic acid;
   (ii) a dried antimicrobial material, wherein the antimicrobial material is produced by drying the whole bulb or whole clove of the plant *Allium sativum*, to form a grannular or powdered antimicrobiol material, said antimicrobial material comprising alliin and alliinase and being substantially free of allicin; and
   (iii) a carrier which is unaffected by culture growth of pathogenic microorganisms thereon.

2. A composition according to claim 1, wherein said Lactobacillus is *Lactobacillus acidophilus* or *Lactobacillus plantarum*.

3. A composition according to claim 1, wherein said Enterococcus is *Enterococcus faecium*.

4. A composition according to claim 1, wherein said antimicrobial material is derived from the plant *Allium sativum* by freeze-drying whole cloves, or whole cloves in which the scar at the end has been cut off.

5. A composition according to claim 1, wherein said non-pathogenic microorganisms are freeze-dried.

6. A method of simultaneously inhibiting propagation of pathogenic microorganisms and promoting colonization of non-pathogenic microorganisms in the gastrointestinal tract of a human or non-human animal, which comprises orally administering an effective amount of an antimicrobial composition to said animal, wherein said antimicrobial composition comprises:
   a) an effective amount of freeze-dried cloves of in *Allium sativum*, or freeze-dried cloves of *Allium sativum* having the scar at the end removed, and being substantially free of allicin and
   b) an amount of non-pathogenic microorganisms selected form the group consisting of Lactobacillus, Enterococcus and Pediococcus effective to colonize the gastrointestinal tract of said animal, wherein said non-pathogenic microorganisms
      i) attach to the apithelial tissue of the small intestine of said animal;
      ii) resist at least 3% (w/w) bile salts;
      iii) have a doubling time of less than two hours in vitro, and
      iv) are homofermentative or heterofermentative lactic acid producers with greater than 40% by molarity of the acid produced being lactic acid,
   and wherein oral administration of said antimicrobial composition causes the simultaneous inhibition of propagation of pathogenic microorganisms in the gastrointestinal tract and promotion of colonization of the gastrointestinal tract of said human or non-human animal with said non-pathogenic microorganisms.

7. The method according to claim 6, wherein of said composition further comprises a carrier.

8. The method according to claim 6, wherein said Lactobacillus is *Lactobacillus acidophilus* or *Lactobacillus plantarum*.

9. The method according to claim 6, wherein said Enterococcus is *Enterococcus faecium*.

10. A method of inhibiting propagation of pathogenic microorganisms and promoting colonization of the gastrointestinal tract of a human or non-human animal with non-pathogenic microorganisms, which comprises orally administering:
    a) an effective amount of an antimicrobial material to said animal so that the orally administered antimicrobial material reaches said gastrointestinal tract and acts to inhibit pathogenic microorganisms present in the animal, wherein said antimicrobial material comprises freeze-dried cloves of *Allium sativum*, or freeze-dried cloves of *Allium sativum* in which the scar at the end has been cut-off, wherein the cloves were freeze-dried to produce an antimicrobial material comprising alliin and alliinase and being substantially free of allicin, and
    b) an effective amount of a composition comprising non-pathogenic microorganisms of the genera Lactobacillus, Enterococcus or Pediococcus effective to colonize the gastrointestinal tract and wherein said non-pathogenic microorganisms
      i) attach to the epithelial tissue of the small intestine of said animal;
      ii) resist at least 3% (w/w) bile salts;
      iii) have a doubling time of less than two hours in vitro, and
      iv) are homofermentative or heterofermentative lactic acid producers with greater than 40% by molarity of the acid produced being lactic acid,
    wherein the oral administration of said antimicrobial material and said composition causes the simultaneous selective inhibition of propagation of said pathogenic microorganisms in the gastrointestinal tract and the selective propagation of said non-pathogenic microorganisms in said tract.

11. The method according to claim 10, wherein said Lactobacillus is *Lactobacillus acidophilus*, or *Lactobacillus plantarum*.

12. The method according to claim 11, wherein said Enterococcus is *Enterococcus faecium*.

* * * * *